(12) United States Patent
Miller et al.

(10) Patent No.: US 9,254,274 B2
(45) Date of Patent: Feb. 9, 2016

(54) METHOD OF TREATING TOURETTE'S DISORDER WITH GABA-AMINOTRANSFERASE INACTIVATORS

(71) Applicants: CATALYST PHARMACEUTICAL PARTNERS, Coral Gables, FL (US); NEW YORK UNIVERSITY, New York, NY (US); THE FEINSTEIN INSTITUTE FOR MEDICAL RESEARCH, Manhasset, NY (US)

(72) Inventors: Steven Miller, Corona, CA (US); Jonathan D. Brodie, Old Greenwich, CT (US); Stephen Dewey, Manorville, NY (US)

(73) Assignees: Catalyst Pharmaceutical Partners, Inc., Coral Gables, FL (US); New York University, New York, NY (US); Feinstein Institute for Medical Research, Manhasset, NY (US)

( * ) Notice: Subject to any disclaimer, the term of this patent is extended or adjusted under 35 U.S.C. 154(b) by 10 days.

(21) Appl. No.: 14/340,749

(22) Filed: Jul. 25, 2014

(65) Prior Publication Data

US 2014/0336256 A1 Nov. 13, 2014

Related U.S. Application Data

(63) Continuation-in-part of application No. PCT/US2013/022054, filed on Jan. 18, 2013.

(60) Provisional application No. 61/591,419, filed on Jan. 27, 2012.

(51) Int. Cl.
| | |
|---|---|
| *A61K 31/13* | (2006.01) |
| *A61K 31/131* | (2006.01) |
| *A61K 31/195* | (2006.01) |
| *A61K 31/197* | (2006.01) |

(52) U.S. Cl.
CPC ............... *A61K 31/131* (2013.01); *A61K 31/13* (2013.01); *A61K 31/195* (2013.01); *A61K 31/197* (2013.01)

(58) Field of Classification Search
CPC ...................................................... A61K 31/13
USPC .......................................................... 514/561
See application file for complete search history.

(56) References Cited

U.S. PATENT DOCUMENTS

| | | |
|---|---|---|
| 6,794,413 B1 | 9/2004 | Silverman |
| 2011/0207718 A1 | 8/2011 | Bird |

FOREIGN PATENT DOCUMENTS

WO 2011/106692 A2 9/2011

OTHER PUBLICATIONS

Supplemental European Search Report dated Aug. 5, 2015, Application No. 13741452.0-1453 / 2806867—PCT/US2013/022054.
Fernandez-Jaen A et al: "An open-label, prospective study of levetiracetam in children and adolescentes with Tourette syndrome", European Journal of Paediatric Neurology, Saunders, Philadelphia, US, vol. 13, No. 6, Nov. 1, 2009, pp. 541-545, XP026714454, ISSN: 1090-3798, DOI: 10.1016/J.EJPN.2008.12.006 [retrieved on Feb. 10, 2009] * abstract * p. 542, col. 1, paragraph 1-3.
Awaad et al: "P1.001 Double-blind controlled randomized study of the use of levetiracetam to treat tics in children and adolescents with Tourette syndrome", Parkinsonism and Related Disorders, Elsevier Science, Oxford, GB, vol. 15, Dec. 1, 2009, p. S29, XP026805563, ISSN: 1353-8020 [retrieved on Dec. 1, 2009] the whole document.
Janik P et al: "P1.003 Glutamic acid to gamma-aminobutyric acid level proportion in Tourette syndrome patients is higher than in controls", Parkinsonism and Related Disorders, Elsevier Science, Oxford, GB, vol. 15, Dec. 1, 2009, pp. S29-S30, XP026805565, ISSN: 1353-8020 [retrieved on Dec. 1, 2009] the whole document.
Mantovani et al. GABAA autoreceptors enhance GABA release from human neocortex: towards a mechanism for high-frequency stimulation (HFS) in brain?. Naunyn-Schmied Arch Pharmacol., 2009, vol. 380, pp. 45-58. [Retrieved from the internet on Mar. 13, 2013 from the URL:<http://material.bccn.uni-freiburg.de>] abstract; p. 46, col. 1, para 1-col. 2, para 1; p. 51. col. 2, para 4-p. 52, col. 2, para 2; Fig 5; p. 56. col. 2, para 2.
Pan et al. 'Design, Synthesis, and Biological Activity of a Difluoro-Substituted, Conformationally Rigid Vigabatrin Analogue as a Potent gamma-Aminobutyric Acid Aminotransferase Inhibitor', J. Med. Chem. 2003, vol. 46, pp. 5292-5293. [Retrieved from the Internet on Mar. 13, 2013 from the URL:<http:I/pubs.acs.org/doi/abs/10.1021/jm034162s>] p. 5292, col. 1, para 3-col. 2. para 1; p. 5293, Scheme 2.
International Search Report and Written Opinion, dated Apr. 5, 2013, for International Application No. PCT/US13/22054, International filed Jan. 18, 2013.

*Primary Examiner* — Raymond Henley, III
(74) *Attorney, Agent, or Firm* — Keller Life Science Law, PA; Michael J. Keller (57) ABSTRACT

The present invention is a method of treating Tourette's Disorder (TD) using GABA ergic drugs that elevate the amount of stored presynaptic GABA and do not significantly increase GABA tone (a continuous background level of GABA signaling) in the brain. The administration of vigabatrin and/or (1S,3S)-3-amino-4-difluoromethylenyl-1-cyclopentanoic acid hydrochloride salt is expressly contemplated.

37 Claims, 1 Drawing Sheet

METHOD OF TREATING TOURETTE'S DISORDER WITH GABA-AMINOTRANSFERASE INACTIVATORS

PRIORITY CLAIM

This application claims priority under 35 U.S.C. 371 and is a continuation-in part of International patent application no. PCT/US13/22054, filed Jan. 18, 2013 which claims the benefit of Provisional patent application No. 61/591,419 filed on Jan. 27, 2012, the contents of which are expressly incorporated by reference. All references cited herein are expressly incorporated by reference.

SUMMARY OF THE INVENTION

The present invention is a method of treating Tourette's Disorder (TD) using GABA-ergic drugs, including GABA-aminotransferase inactivator drugs, that significantly increase presynaptically stored GABA but do not significantly increase GABA tone (a continuous background level of GABA signaling) in the brain. The administration of vigabatrin and/or (1S,3S)-3-amino-4-difluoromethylenyl-1-cyclopentanoic acid hydrochloride salt are expressly contemplated.

BACKGROUND

The contents of all cited references are expressly incorporated by reference. Tourette's Disorder (TD), thought to be a lifelong condition, is a childhood onset neuropsychiatric disorder characterized by multiple motor and vocal tics that is associated with considerable disability and reduction in quality of life (DSM IV-TR, 2000). The majority of clinically referred youth with TD also meet criteria for comorbid Obsessive-Compulsive Disorder (OCD) and Attention Deficit Hyperactivity Disorder (ADHD), and young adults meet criteria for additional anxiety, mood and substance use disorders. (Coffey B, Biederman J, Spencer T et al 2000; Coffey, Miguel, Biederman, JNMD 1998). Research in the past decade suggests peak tic severity occurs at about age 10-11 years with improvement into adolescence, and gradual attenuation of tics by early adulthood. However, a substantial minority of individuals with TD continue to experience disabling tic symptoms throughout their lives.

Common motor tics include, but are not limited to: eye blinking, coughing, throat clearing, sniffing, and facial movements. Simple vocal tics include involuntary inarticulate noises while complex vocal tics include syllables, words, phrases and in extreme cases includes derogatory remarks and profanity (coprolalia). The disorder often accompanies other disorders such as attention deficit hyperactivity disorder and obsessive compulsive disorder.

Tourette's Disorder is known to have genetic and environmental causes although the exact mode of inheritance is unknown. Diagnosis under the DSM-IV includes the presence of multiple motor tics and at least once vocal tic for greater than one year; onset prior to age 18; and frequent tics which cause distress or impairment which are not secondary to another condition.

A discussion of current therapies for treatment of Tourette's disorder can be found in Lyon, Gholson G, et al. Tourette's Disorder, Current Treatment Options in Neurology, 12: 274-286 (2010). Treatment of Tourette's Disorder includes administration of the antihypertensive alpha-2-agonists clonidine and guanfacine, administration of atypical neuroleptics such as olanzapine, ziprasidone, and risperidone; classic neuroleptics such as haloperidol, pimozide; tetrabenzanine; agents which deplete presynaptic dopamine and serotonin stores and which block postsynaptic dopamine receptors such as tetrabenazine. Benzodiazapines also appear in the literature but have not been subject to controlled clinical trials. Motor tics have also been treated with botulinum toxin.

Emerging therapies currently undergoing studies include levetiracetam, topiramate, the GABA-B agonist baclofen, and the dopamine agonists pergolide, cabergoline, ropinirole and pramipexole.

Clonidine and guanfacine, while having limited long term side effects limited largely to sedation, fatigue and somnolence, are only about 30% to 35% effective at reducing symptoms. The neuroleptic antipsychotics have a variable risk of extrapyramidal side effects that include akathisia, tardive dyskinesia and dystonias as well as affective constriction and cognitive blunting. The only formally approved treatments for TD are haloperidol and pimozide, which are typical neuroleptic agents known to have these adverse effects (Scahill et al 2006). Given the significant potential for adverse effects associated with use of typical neuroleptics, better tolerated and efficacious alternatives are needed.

Tics are thought to result from disinhibition of the cortico-striatal-thalamo-cortical tracts, pathways involved in habit formation, linking the basal ganglia, thalamus and frontal cortex. (Leckman et al JCAP, 2010). Multiple converging lines of evidence, including clinical trials with D2 dopamine receptor antagonists and in vivo neuroimaging studies of DAT binding in the striatum, suggest that TD is a disorder of dopaminergic transmission, conceptualized as an excess of nigrostriatal dopamine activity through dysfunctional presynaptic receptors or hyperfunctional dopamine innervation. More recent evidence has suggested that other neurotransmitters, specifically GABA, may also play a significant role in the pathophysiology of TD, particularly with regard to GABAergic neurons' impact on dopaminergic pathways. GABA neurons are present in the "direct pathway" of medium spiny neurons projecting to the internal segment of the globus pallidus and substantia nigra, and in the "indirect pathway" from the striatum to the external segment of the globus pallidus and on to the internal segment (Leckman et al JCAP 2010). Several postmortem studies of TD patients identified marked decreased in number and density of GABAergic parvalbumin-positive neurons in the basal ganglia, for example, more than 50% reduction in FSINs in caudate and 30-40% reduction in putamen. (Kalanithi et al., 2005; Kataoka et al., 2010). Another study reported more than 50% reduction of GABAergic Fast spiking GABAergic interneurons ("FSINs") and loss of TANs (tonically active neurons). In addition, preliminary findings from a Tourette Syndrome Association sponsored study of GABA brain concentrations in adolescents with TD indicate significantly decreased anterior cingulated cortex (ACC) and striatal GABA in adolescents with TD relative to healthy controls (Gabbay and Coffey, 2011).

FSINs and cholinergic tonically active neurons (TANs) are thought to play an important role in modulation of tics and habit learning. FSINs are reported to show characteristic irregular bursting with stable intra-burst frequencies similar to tic patterns (Peterson and Leckman, 1998) TANs are reported to be sensitive to salient perceptual signals and respond to dopaminergic input from the substantia nigra.

To the extent that tics are a likely manifestation of phasic dopamine (DA) activity, clinical experience with other conditions characterized by such properties, e.g. cocaine and methamphetamine addiction would suggest that vigabatrin may be effective in reducing tics. Vigabatrin, at doses that are FDA approved for treatment of epilepsy is well tolerated and should be well tolerated for the treatment of Tourette's Disorder.

Vigabatrin (γ-vinyl GABA) has not previously been used for treatment of Tourettes Disorder but it has been used for treatment of neurological disorders. Vigabatrin is sold worldwide under the trademark Sabril™ for treatment of epilepsy. Vigabatrin has been studied for treatment of drug addiction. Vigabatrin's well known mechanism of action is the irreversible inhibition of gamma-aminobutyric acid-aminotransferase (GABA-AT). This enzyme is responsible for the catabolism of gamma aminobutyric acid (GABA) in the brain. Inhibition of this enzyme results in an elevation of brain levels of GABA. The elevation of brain GABA (the brain's primary inhibitory neurotransmitter) results in a decrease of neuron excitability and as such reduces uncontrolled firing of neurons, which leads to a reduction in epileptic seizures.

U.S. Pat. Nos. 7,381,748 and 6,794,413, which are incorporated herein by reference disclose the compound (1S,3S)-3-amino-4-difluoromethylenyl-1-cyclopentanoic acid. The literature has shown that (1S,3S)-3-amino-4-difluoromethylenyl-1-cyclopentanoic acid is approximately 52 times more potent as a mechanism-based inactivator of γ-aminobutyric acid aminotransferase (GABA-AT) than the anticonvulsant drug and GABA-AT inactivator vigabatrin (Sabril™) under nonoptimal conditions (conditions other than physiological pH and temperature) (Pan, Y.; Qiu, J.; Silverman, R. B. Design, Synthesis, and Biological Activity of a Difluoro-substituted, Conformationally-rigid Vigabatrin Analogue As a Potent γ-Aminobutyric Acid Aminotransferase Inhibitor. *J. Med. Chem.* 2003, 46, 5292-5293).

The phrase "pharmaceutically acceptable salt(s)", as used herein, means those salts of compounds of the invention that are safe and effective for use in mammals and that possess the desired biological activity. Pharmaceutically acceptable salts include salts of acidic or basic groups present in vigabatrin or (1S,3S)-3-amino-4-difluoromethylenyl-1-cyclopentanoic acid. Suitable acids include: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid), salicylic acid, sebacic acid, stearic acid, succinic acid, sulfuric acid, tartaric acid, thiocyanic acid, toluenesulfonic acid, undecylenic acid. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. (1S,3S)-3-amino-4-difluoromethylenyl-1-cyclopentanoic acid. can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 J. Pharm Sci 1-19 (1977) and P. Heinrich Stahl, Camille G. Wermuth (Eds.) *Handbook of Pharmaceutical Salts: Properties, Selection, and Use*, Wiley, (2002), the contents of which are expressly incorporated herein by reference.

U.S. Pat. Nos. 6,906,099; 6,890,951; 6,828,349; 6,593,367; 6,541,520; 6,395,783; 6,323,239; and 6,057,368 which describe and/or claim the use of vigabatrin in the treatment of addiction from cocaine, nicotine, methamphetamine, morphine, heroin, ethanol, phencyclidine, methylene-dioxymethamphetamine, and/or PCP, the contents of such patents are expressly incorporated herein by reference.

U.S. Pat. No. 6,462,084 describes and/or claims the use of vigabatrin in the treatment of obsessive compulsive disorders including general anxiety disorder, pathological or compulsive gambling disorder, compulsive eating (obesity), body dysmorphic disorder, hypochondriasis, pathologic grooming conditions, kleptomania, pyromania, attention deficit hyperactivity disorder and impulse control disorders. The contents of U.S. Pat. No. 6,462,084 is expressly incorporated herein by reference.

U.S. Pat. No. 6,939,876 describes and/or claims the use of vigabatrin in the treatment to prevent addiction to opioid analgesics by co administration of vigabatrin. The contents of U.S. Pat. No. 6,939,876 is expressly incorporated herein by reference.

GABA-ergic drugs are those which improve synaptic concentration or activity of GABA or increase the activation of GABA receptors, directly or indirectly. These drugs as a family have been used to treat a wide variety of nervous system disorders including fibromyalgia, neuropathy, migraines related to epilepsy, restless leg syndrome, and post traumatic distress disorder, anxiety, and insomnia. GABA-ergic drugs include $GABA_A$ and $GABA_B$ receptor ligands, GABA reuptake inhibitors, GABA aminotransferase inactivators and inhibitors, GABA analogs, or molecules containing GABA itself. Currently marketed GABA-ergic drugs that could possibly be useful for the treatment of Tourette's Disorder include valproate and its derivatives, vigabatrin, pregabalin, gabapentin and tiagabine.

Once GABA-AT (GABA-aminotransferase) has been inactivated, it takes a number of days for the brain to synthesize new GABA-AT to replace the inactivated enzyme. Researchers have demonstrated (Petroff, Ognen A. C.; Rothman, Douglas L.; "Measuring Human Brain GABA In Vivo, Effects of GABA-Transaminase Inhibition with Vigabatrin", Molecular Neurobiology, 1998, 16(1), 97-121) that brain GABA levels remain substantially elevated for several days after administration of a single dose of vigabatrin. This observation is consistent with the assertion that it takes several days for the brain to restore the GABA-AT activity.

It is an object of the present invention to treat Tourette's Disorder by delivering a GABA aminotransferase inactivator to a patient in need thereof.

It is an object of this invention to treat patients having Tourette's Disorder using an irreversible inactivator of GABA aminotransferase.

It is an object of this invention to use Vigabatrin and its derivatives to treat Tourette's Disorder.

It is an object of the present invention to treat Tourette's Disorder using (1S,3S)-3-amino-4-difluoromethylenyl-1-cyclopentanoic acid and its pharmaceutically acceptable salts.

DETAILED DESCRIPTION OF THE INVENTION

The present invention is a method of treating Tourette's Disorder (TD) using GABA-ergic drugs that do not significantly increase GABA tone (a continuous background level of GABA signaling) in the brain. The administration of vigabatrin or (1S,3S)-3-amino-4-difluoromethylenyl-1-cyclopentanoic acid hydrochloride salt are expressly contemplated.

The compositions used in the present method can be administered systemically by the parenteral and enteral routes which also includes controlled release delivery systems. For example, intravenously, sublingual, or intraperitoneal (i.p.). Intravenous or intraperitoneal administration can be accomplished by mixing the active agent in a suitable pharmaceutical carrier (vehicle) or formulation as understood by practitioners in the art. While immediate release orally delivered dosage forms are identified in the examples, controlled or delayed release dosage forms can readily be created using means well known in the art.

Example 1

Treatment of Tourettes Using Vigabatrin

Study (Treatment) Objectives:

The aims of this study are to 1) explore proof of concept that vigabatrin will reduce tics, and 2) to obtain systematic data regarding dosing, safety and tolerability of vigabatrin in young adults with treatment refractory TD. This study will obtain preliminary data to estimate the effect size for tics using Cohen's d, calculating the difference between the two means (baseline and endpoint scores on the Y-GTSS), divided by the standard deviation of the difference.

Tourette's Disorder (TD), thought to be a lifelong condition, is a childhood onset neuropsychiatric disorder characterized by multiple motor and vocal tics that is associated with considerable disability and reduction in quality of life (DSM IV-TR, 2000). The majority of clinically referred youth with TD also meet criteria for comorbid Obsessive-Compulsive Disorder (OCD) and Attention Deficit Hyperactivity Disorder (ADHD), and young adults meet criteria for additional anxiety, mood and substance use disorders. (Coffey B, Biederman J, Spencer T et al 2000; Coffey, Miguel, Biederman, JNMD 1998). Research in the past decade suggests peak tic severity occurs at about age 10-11 years with improvement into adolescence, and gradual attenuation of tics by early adulthood. However, a substantial minority of individuals with TD continue to experience disabling tic symptoms throughout their lives. The only formally approved treatments for TD are haloperidol and pimozide, typical neuroleptic agents known to have significant and unwanted adverse effects such as tardive dyskinesia, weight gain and cognitive blunting (Scahill et al 2006). Given the significant potential for adverse effects associated with use of typical neuroleptics, better tolerated and efficacious alternatives are needed.

Mechanism of Action of Vigabatrin

Vigabatrin inhibits GABA-aminotransferase (GABA-AT), the enzyme responsible for the catabolism of GABA in the brain. Unlike the variety of GABA-ergic drugs that have been tried for treatment of tics (i.e. baclofen) and which have met with very limited success, vigabatrin does not significantly raise GABA tone (a continuous background level of GABA signaling) in the brain. Instead, the inhibition of GABA-AT results in a build-up of GABA in presynaptic terminals of GABA-ergic neurons. These large stores of GABA, packaged in vesicles, are released when the GABA-ergic neuron is depolarized. As GABA-AT inhibition significantly increases the stores of GABA in the presynaptic terminal, when the neuron depolarizes and releases GABA, the resulting GABA-ergic "signal" is significantly increased. In other words, vigabatrin effectively "amplifies" the GABA-ergic signaling mechanisms without significantly raising GABA-tone.

In the case of GABA-ergic drugs that raise GABA tone (either by direct action on GABA receptors (i.e. baclofen) or by inhibition of GABA reuptake (i.e. tiagabine), increased GABA tone initiates adaptive mechanisms in the brain that lead to tolerance to the drug and an attenuation of the drug's effects over time, particularly in the dopaminergic neurons. Furthermore, continuous activation of GABA receptors leads to a variety of central nervous system (CNS) adverse effects. In contrast, vigabatrin amplifies the GABA-ergic signaling without triggering adaptations to changes in GABA tone, and also has minimal CNS adverse effects, as there is not continuous elevated GABA signaling. It is for this reason that vigabatrin has a very benign CNS adverse effects profile, and why there is no significant development of tolerance to the effects of the drug.

The action of vigabatrin is transient in nature. "Amplified" GABA signals are sent to the dopaminergic neuron, but the GABA signaling duration is not long enough to activate the compensatory mechanisms that blunt the dopaminergic neurons' response to GABA.

Taken together, given putative evidence that hyperfunction of dopaminergic neurotransmission and reduction/dysfunction of phasic GABAergic neurons in the CTSC tracts may underlie the pathophysiology of TD, vigabatrin has theoretical potential to ameliorate tics in patients with TD (Albin, 2004). Vigabatrin's activity-dependent release of presynaptic GABA quenches the phasic increase in DA, and thus makes it potentially uniquely beneficial to patients with TD. However, the lack of efficacy data and limited safety data in this population makes it advisable to begin with a small, open pilot study of safety and efficacy prior to conducting double-blind placebo-controlled trials.

Vigabatrin is preferably administered at a dose between 0.5 and 4 grams per day and most preferably administered between 1 and 3 grams per day.

Summary of Study Design:

This is an open label investigation to obtain preliminary data regarding dosage and tolerability of vigabatrin in 6-10 subjects at least 18 years of age who meet Diagnostic and Statistical Manual of Mental Disorders, Text Revision (DSM-IV-TR, 2000) criteria for TD and who have had unsatisfactory response to prior treatments. Our goal is to obtain preliminary data on effect size for tics using Cohen's d, calculating the difference between the two means (baseline and endpoint scores on the Yale Global Tic Severity Scale (Y-GTSS), divided by the standard deviation of the difference.

Summary of Inclusion and Exclusion Criteria:

Subjects must be physically healthy, of at least average intelligence, and have no other significant medical or comorbid psychiatric disorders that are the primary focus of treatment.

Inclusion Criteria:

Subjects will be eligible for inclusion in this study if they meet all of the following criteria:
1. Subjects must be 18 years of age (inclusive) when informed consent is obtained.
2. Subjects must meet full DSM-IV diagnostic criteria for TD by clinical interview on examination by a physician investigator, and confirmed by the Structured Clinical Interview for DSM (SCID-CT) for clinical trials.
3. Subjects will have failed to respond to an adequate trial, as determined by the investigator, of clonidine, guanfacine, and a first generation (typical) and second generation (atypical) neuroleptic medication in the past.
4. Tics are causing significant distress or impairment, as determined by the subject and principal investigator, on the current treatment regimen.
5. Laboratory results, including serum chemistries, hematology, and urinalysis, must show no significant abnormalities (significant is defined as laboratory values requiring acute medical intervention).
6. Subjects will not undergo formal IQ testing, but must be of normal intelligence in the judgment of the investigator.
7. Subjects must possess an educational level, degree of understanding and command of the English language to enable them to communicate suitably with the investigators and study coordinator, and to understand the nature of the study.
8. Subjects must be considered reliable.
9. Written informed consent of subjects is obtained.

Exclusion Criteria:

Subjects will be excluded from the study for any of the following reasons:
1. Subjects with organic brain disease, for example, traumatic brain injury residua.
2. Subjects meeting criteria for mental retardation as defined by the DSM-IV-TR
3. Subjects with a history of seizure disorder (other than febrile seizure).
4. Subjects with history of Sydenham's Chorea.
5. Subjects with autism, schizophrenia, other psychotic disorder, or bipolar disorder.
6. Subjects with a primary diagnosis of a major mood disorder that requires ongoing psychiatric treatment.
7. Subjects with a neurological disorder other than a tic disorder.
8. Subjects with a major medical illness.
9. Female subjects who are unwilling to use birth control or who are pregnant, as determined by serum pregnancy test at baseline assessment, or lactating.
10. Subjects who have a past or current history of substance dependence and/or a current history of substance abuse or who fail baseline toxicology screen.
11. Subjects who have any clinically significant abnormal laboratory result at baseline screening including EKG, or blood tests.
12. Subjects who, in the opinion of the investigator, are unsuitable in any other way to participate in this study.
13. Subjects currently being treated for epilepsy with vigabtrin (Sabril™)

Proposed Visit Schedule:

The trial will last approximately 8 weeks and include 8 visits. Assessment visits will take place at baseline (Visit 1), and treatment weeks 0 (visit 2), 1 (visit 3), 2 (visit 4), 3 (visit 5) 4 (visit 6), 6 (visit 7) and 8 (visit 8).

Visit 1 (Baseline Assessment and Medication Washout):

After pre-screening, at this visit written consent, baseline physical exam, vital signs, height and weight, EKG, and laboratory assessment will be conducted. Clinical assessment will consist of clinical evaluation by the co-principal investigator experienced in the evaluation and treatment of Tourette's and tic disorders (BC), and semi-structured diagnostic interview (SCID-CT).

Taper and Discontinuation of Previous Tic Medication.

Current tic medication will be tapered and discontinued. Visit 1 may be divided into additional visits (i.e. 1A, 1B) to taper and withdraw previous tic medication if needed. Subjects must be off all other tic medications prior to beginning treatment with vigabatrin by Study Visit 2. If feasible, subjects should be off clonidine or guanfacine for at least 2 weeks, and typical or atypical neuroleptics for at least 4 weeks prior to starting the study medication. However, if it is clinically unfeasible, in the judgment of the investigator, for the subject to remain off previous tic medication for the duration of the discontinuation phase, vigabatrin may be initiated before the end of the 2-4 week period, with agreement of the subject and investigator.

In regard to the tapering and discontinuation of a previous medications for TD, clinically unfeasible is defined as: in the judgment of investigator, the subject's tics would be highly likely to cause increased distress or impairment to the subject without treatment, and initiation of treatment with a replacement therapy, in this case vigabatrin, would be indicated.

Medication for Psychiatric Comorbid Conditions.

Subjects on medications for a comorbid condition (such as a stimulant for ADHD or a selective serotonin reuptake inhibitor (SSRI) for OCD) may remain on the medication during the study, but will agree to remain on the same dosage throughout the duration of the study.

Baseline Measures:

The following instruments will be used to assess diagnosis and symptom severity at baseline:
a) SCID-CT. A clinician administered, semi-structured diagnostic interview specifically developed for use in clinical trials with adults
b) Yale Global Tic Severity Scale (Y-GTSS) (Leckman et al, 1989). The primary outcome measure for tic assessment is this investigator administered Global Severity score (sum of Total Tic score and TD Impairment score) on the Y-GTSS. It includes measures of tic frequency and severity and is widely used in drug efficacy trials involving TD.
c) Yale-Brown Obsessive Compulsive Scale (Y-BOCS) (Goodman et al, 1989). The Y-BOCS is a primary outcome measure of OCD symptoms and is rated by a study investigator.
d) Clinical Global Impression for Tics (Tics-CGI) (Leckman et al, 1988), for ADHD (ADHD-CGI), and for OCD (OCD-CGI) (Guy et al, 1976). Rated by the investigator. Global Improvement (1=very much improved, to 7=very much worse) scales. At intake, only the severity can be rated. In subsequent assessments, both severity and improvement will be rated. A CGI improvement of 1 (very much) or 2 (much) improved is considered to be an acceptable response to acute treatment as is a clinical severity rating of ≤3.
e) DSM-IV-TR Global Assessment of Functioning Scale (GAF) (APA DSM-IV-TR, 2000). The investigator-rated GAF ranges from 1-100, with scores over 70 indicating normal adjustment, and below 60, clinically significant impairment.
f) Hamilton Depression Scale. A clinician-rated scale used as a screening and diagnostic tool and a measure of severity of depression in adults, which has been widely used in clinical trials of young adults with MDD.

g) Hamilton Anxiety Scale. A clinician-rated scale used as a screening and diagnostic tool and a measure of severity of depression in adults, which has been widely used in clinical trials of young adults with MDD.

h) Conners Adult ADHD Rating Scale (CAARS:SL) Systematic self-report of ADHD symptoms in adults.

i) Adverse Events Form (SMURF) is completed at every visit to document all adverse events that occur during the study.

j) Demographics: Demographics and family history information are collected systematically during the Screening/Baseline Phase.

k) Vital signs, Weight and Height (pulse, blood pressure, weight, and height) will be assessed at every visit.

l) Abnormal Involuntary Movement Scale (AIMS) An investigator rated scale of abnormal involuntary movements including tardive dyskinesia.

m) Opthalmological evaluation including visual fields testing

Visit 2 (Treatment Week 0):

Clinical Assessment (See Table 1). Subjects will undergo a repeat assessment of all baseline rating scales, except for the SCID-CT, physical exam and Demographics Assessment. Vital signs, weight, height, AIMS and adverse events will be assessed at every visit.

Subjects will be started on vigabatrin according to dosing plan 1 (see Table 2). Based on the known dose-effects profile of vigabatrin, dosing plan 1 is the most clinically useful dosing regimen. Due to the mechanism of action of vigabatrin and the relatively long period of time (several days) for the denovo resynthesis of GABA-aminotransferase, it is envisioned that dosing regimens using smaller doses of vigabatrin will be effective in the treatment of Tourette's disorder because less drug would be effective at maintaining a low GABA-aminotransferase activity after initial depletion of enzyme activity. Alternative dosing plans envisioned to be effective can also be found in Table 2. However, due to the known somnolence side effect upon initiation of treatment, and the known dose at which this effect is observed, the initial dose on week zero is not equally proportional to the maximum dose utilized during the study for all dosing plans.

Visit 3 (Treatment Week 1):

Clinical Reassessment (see Table 1). Vital signs, weight, height, AIMS and adverse events will be assessed at each visit. Visit 3 will also include: Yale Global Tic Severity Scale (Y-GTSS), Clinical Global Impression for Tics (Tic-CGI), ADHD (ADHD-CGI) and OCD (OCD-CGI), Global Assessment of Functioning Scale (GAF)

Visit 4 (Treatment Week 2):

Clinical reassessment (See Table 1). Vital signs, weight, height, AIMS and adverse events will be assessed at each visit. Visit 4 will further include Yale Global Tic Severity Scale (Y-GTSS), Clinical Global Impression for Tics (Tics-CGI), ADHD (ADHD-CGI) and OCD (OCD-CGI), Y-BOCS, CAARS, and GAF.

Visit 5: (Treatment Week 3):

Clinical Reassessment (See Table 1). Vital signs, weight, height, AIMS and adverse events will be assessed at each visit. Visit 5 will further include Yale Global Tic Severity Scale (Y-GTSS); Clinical Global Impression for TS (TS-CGI), ADHD (ADHD-CGI) and OCD (OCD-CGI); GAF; Adverse Events Form (SMURF)

Visit 6 (Treatment Week 4)

Clinical Reassessment (See Table 1). Vital signs, weight, height, AIMS and adverse events will be assessed at each visit. Visit 6 will further include: Yale Global Tic Severity Scale (Y-GTSS); Yale-Brown Obsessive Compulsive Scale (Y-BOCS), CAARS; Clinical Global Impression for Tics (Tics-CGI), ADHD (ADHD-CGI) and OCD (OCD-CGI), GAF, Adverse Events Form (SMURF)

Visit 7 (Treatment Week 6)

Clinical Reassessment (See Table 1). Vital signs, weight, height, AIMS and adverse events will be assessed at each visit. Visit 7 will also include: Yale Global Tic Severity Scale (Y-GTSS), Clinical Global Impression for Tics (Tics-CGI), ADHD (ADHD-CGI) and OCD (OCD-CGI), and GAF.

Visit 8 (Treatment Week 8)

Clinical Assessment (See Table 1). Subjects will undergo an endpoint, repeat assessment of all baseline rating scales, except for the SCID-CT and Demographics Assessment. Endpoint outcome measures will be calculated.

TABLE 1

TASKS BY VISIT

| Assessment Tools | Screen Phase Baseline visit 1 | Week 0 visit 2 | Week 1 visit 3 | Week 2 visit 4 | Week 3 visit 5 | Week 4 visit 6 | Week 6 visit 7 | Week 8 visit 8 |
|---|---|---|---|---|---|---|---|---|
| SCID-CT | X | | | | | | | |
| Y-GTSS | X | X | X | X | X | X | X | X |
| Y-BOCS | X | X | | X | | X | | X |
| CGI-Tics | X | X | X | X | X | X | X | X |
| CGI-OCD | X | X | X | X | X | X | X | X |
| CGI-ADHD | X | X | X | X | X | X | X | X |
| GAF | X | X | X | X | X | X | X | X |
| HAM-D | X | X | | | | | | X |
| HAM-A | X | X | | | | | | X |
| CAARS | X | X | | X | | X | | X |
| Adverse Events | X | X | X | X | X | X | X | X |
| Physical Exam | X | | | | | | | |
| Weight and Height | X | X | X | X | X | X | X | X |
| Blood Tests: CBC, Metabolic Panel including | X | | | | | | | X |

TABLE 1-continued

TASKS BY VISIT

| Assessment Tools | Screen Phase Baseline visit 1 | Week 0 visit 2 | Week 1 visit 3 | Week 2 visit 4 | Week 3 visit 5 | Week 4 visit 6 | Week 6 visit 7 | Week 8 visit 8 |
|---|---|---|---|---|---|---|---|---|
| Liver Function Tests, Cholesterol, Triglycerides, Fasting Blood Sugar and Prolactin | | | | | | | | |
| ECG | X | | | | | | X | |
| Urine toxic screen | X | | | | | | | |
| Pregnancy test (females only) | X | | | | | | | |
| Vital Signs | X | X | X | X | X | X | X | X |
| AIMS | X | X | X | X | X | X | X | X |

TABLE 2

DRUG DOSING PLANS. Dosing is envisioned to be administration of the complete daily dose at bed time (hs)

Dosing plans, grams per day of vigabatrin

| Study Week | Plan #1 | Plan #2 | Plan #3 | Plan #4 | Plan #5 |
|---|---|---|---|---|---|
| 0 | 1 | 1 | 1 | 0.5 | 1 |
| 1 | 2 | 2 | 1 | 0.5 | 2 |
| 2 | 3 | 2 | 1 | 0.5 | 4 |
| 3 | 3 | 2 | 1 | 0.5 | 4 |
| 4 | 3 | 2 | 1 | 0.5 | 4 |
| 5 | 3 | 2 | 1 | 0.5 | 4 |
| 6 | 3 | 2 | 1 | 0.5 | 4 |
| 7 | 2 | 2 | 1 | 0.5 | 2 |
| 8 | 1 | 1 | 1 | 0.5 | 1 |

Follow-Up:

Subjects enrolled in the study will be eligible for follow-up at the NYU Clinical and Research Program for Tics and Tourette's following completion of the study. Those who show benefit from the medication at the endpoint dosage may have the opportunity to continue treatment, but at a reduced dose and with appropriate follow up testing, including visual fields assessments every four months.

Data Analysis:

As this is a preliminary, open label study to systematically assess safety and basic effects profile, all analyses will be descriptive. Patient characteristics for all individuals enrolled in the study will be summarized.

Analysis of safety data will include all subjects who take at least one dose of study medication. Types and percentages of treatment-emergent, unsolicited adverse effects will be summarized for each visit. Any subject who experiences a serious adverse effect, or who cannot tolerate any adverse effect, will be taken off the medication and removed from the study.

To obtain preliminary data regarding effect size, we will examine mean change from baseline to endpoint on measures of tics (Y-GTSS), We will obtain preliminary data on effect size (ES) for tics using Cohen's d, calculating the difference between the two means (baseline and endpoint scores on the Y-GTSS), divided by the standard deviation of the difference. Exploratory analyses will take place with change from baseline on CGI-Tics Severity, and Y-BOCS, CAARS, Hamilton A and D. Although our mean baseline and endpoint scores are non-independent, if the pooled standard deviation is corrected for the amount of correlation between measures, then the ES estimate will be an overestimate of the actual ES. (Dunlop, Cortina, Vaslow and Burke, 1996). Thus, we will use the original standard deviations.

Minimizing Risk of Intolerable Increase in Tics During Taper and Discontinuation Phase of Previous Tic Medication If tics increase to the point of causing significant distress or impairment to the subject, by clinical judgment of the investigator and subject, appropriate measures will be instituted to reduce the symptoms. Measures to reduce symptoms could include 1) initiation of vigabatrin before the end of the discontinuation phase of previous tic medication if tics worsen during the discontinuation phase, 2) adjustment in dose of vigabatrin as needed during the treatment phase, or 3) removal of the subject from the study if tics worsen on two consecutive treatment visits.

Example 2

Treatment with (1S,3S)-3-amino-4-difluoromethylenyl-1-cyclopentanoic acid hydrochloride salt Study Objectives:

The aims of this study are to 1) explore proof of concept that (1S,3S)-3-amino-4-difluoromethylenyl-1-cyclopentanoic acid hydrochloride salt will reduce tics, and 2) to obtain systematic data regarding dosing, safety and tolerability of (1S,3S)-3-amino-4-difluoromethylenyl-1-cyclopentanoic acid hydrochloride salt in adults with treatment refractory TD. We will obtain preliminary data to estimate the effect size for tic reduction using Cohen's d, calculating the difference between the two means (baseline and endpoint scores on the Y-GTSS), divided by the standard deviation of the difference.

U.S. Pat. Nos. 7,381,748 and 6,794,413, which are incorporated herein by reference disclose the compound (1S,3S)-3-amino-4-difluoromethylenyl-1-cyclopentanoic acid and its salts. The literature has shown that (1S,3S)-3-amino-4-difluoromethylenyl-1-cyclopentanoic acid is approximately 52 times more potent as a mechanism-based inactivator of γ-aminobutyric acid aminotransferase (GABA-AT) than the anticonvulsant drug and GABA-AT inactivator vigabatrin (Sabril™) under nonoptimal conditions (conditions other than physiological pH and temperature) (Pan, Y.; Qiu, J.; Silverman, R. B. Design, Synthesis, and Biological Activity of a Difluoro-substituted, Conformationally-rigid Vigabatrin Analogue As a Potent γ-Aminobutyric Acid Aminotransferase Inhibitor. *J. Med. Chem.* 2003, 46, 5292-5293).

While this example specifies the use of the hydrochloride salt of (1S,3S)-3-amino-4-difluoromethylenyl-1-cyclopentanoic acid, one of skill in the art will appreciate that other pharmaceutically acceptable salts can be substituted for the hydrochloride salt. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. (1S,3S)-3-amino-4-difluoromethylenyl-1-cyclopentanoic acid. forms pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 J. Pharm Sci 1-19 (1977) and P. Heinrich Stahl, Camille G. Wermuth (Eds.) *Handbook of Pharmaceutical Salts: Properties, Selection, and Use*, Wiley, (2002), the contents of which are expressly incorporated herein by reference.

Mechanism of Action of (1S,3S)-3-amino-4-difluoromethylenyl-1-cyclopentanoic acid hydrochloride salt A new synthetic compound, (1S,3S)-3-amino-4-difluoromethylenyl-1-cyclopentanoic acid, was designed as a mechanism-based inactivator of GABA-AT, which could generate a more reactive intermediate along the pathway to attachment to the active site of GABA-AT via a Michael addition (Pan, Y.; Qiu, J.; Silverman, R. B.; Design, Synthesis and biological Activity for a Difluoro-substituted, conformationally-rigid Vigabatrin Analogue As a Potent γ-Aminobutyric Acid Aminotransferase Inhibitor. *J. Med. Chem.* 2003, 46, 5292-5293). In contrast to the high $K_I$ and $K_{inact}$ values (3.2 mM; 0.37 min$^{-1}$, $K_{inact}/K_I$ mM$^{-1}$ min$^{-1}$) reported for vigabatrin as an inactivator of GABA-AT, this new synthetic GABA-AT inactivator has a $K_I$ value of 31 $K_{inact}$ of 0.18 min$^{-1}$, and a $K_{inact}/K_I$ of 5.7 mM-1 min-1. A comparison of the $k_{inact}/K_I$ values (a measure of the efficiency of the inactivator) indicated that (1S,3S)-3-amino-4-difluoromethylenyl-1-cyclopentanoic acid is 186 times more effective as an inactivator of GABA-AT than (S)-vigabatrin under suboptimal, non-physiological conditions (at optimal conditions for substrate turnover, the rate of inactivation is too rapid to measure; these values were obtained at a pH and temperature well below the optimum). Despite irreversibility of the inhibition (i.e. inactivation), the low potency of vigabatrin translates into treatment doses of 1-3 g/day (U.S. Labeling for Sabril™ http://www.lundbeckinc.com/USA/products/CNS/Sabril/sabril_PI_CPS.pdf). Because (1S,3S)-3-amino-4-difluoromethylenyl-1-cyclopentanoic acid displayed superior enzyme inactivation properties compared to vigabatrin, we have carried out further pharmacological studies with (1S,3S)-3-amino-4-difluoromethylenyl-1-cyclopentanoic acid hydrochloride salt. The affinity of (1S,3S)-3-amino-4-difluoromethylenyl-1-cyclopentanoic acid hydrochloride salt at $GABA_A$ and $GABA_B$ receptors and its activity at the $GABA_C$ receptor as well as at four GABA transporter subtypes expressed either endogenously in neurons and astrocytes or recombinantly in mammalian cell lines was determined. Because of the preponderance of data indicating vigabatrin is effective for the treatment of addiction, the previously reported (Fechtner, R; et al.; Short-term Treatment of cocaine and/or Methamphetamine Abuse with Vigabatrin. *Arch. Ophthalmol.* 2006, 124(9), 1257-1262) lack of visual field defect observed for short vigabatrin exposure durations required for the treatment of stimulant addiction, and the relatively short duration of drug exposure needed for addiction treatment, the effect of (1S,3S)-3-amino-4-difluoromethylenyl-1-cyclopentanoic acid hydrochloride salt on cocaine-induced conditioned place preference in rats (an animal model for effectiveness of addiction treatments) also was investigated. Mechanistic similarities between vigabatrin and (1S,3S)-3-amino-4-difluoromethylenyl-1-cyclopentanoic acid hydrochloride salt for the treatment of addiction were also investigated by microPET imaging to measure the ability of (1S,3S)-3-amino-4-difluoromethylenyl-1-cyclopentanoic acid hydrochloride salt to antagonize cocaine-induced increases in synaptic nucleus accumbens dopamine.

While the compound (1S,3S)-3-amino-4-difluoromethylenyl-1-cyclopentanoic acid has been shown to be a GABA aminotransferase inactivator like vigabatrin, surprisingly (1S,3S)-3-amino-4-difluoromethylenyl-1-cyclopentanoic acid hydrochloride salt does not inhibit the reuptake of GABA. As reported in the literature, although vigabatrin is an irreversible inactivator of GABA-AT, its binding to GABA-AT is relatively weak ($K_I$=3.2 mL, $K_{inact}$=0.37, $K_{inact}/K_I$=0.11) (Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293). Dr. Richard Silverman elucidated the mechanism by which vigabatrin inactivates GABA-AT (Burke, James R.; Silverman, Richard B.; "Mechanism of inactivation of γ-aminobutyric acid aminotransferase by the antiepilepsy drug γ-vinyl GABA (vigabatrin)", J. Am. Chem. Soc., 1991, 113(24), 9341-9349) and then set out to develop a new GABA-AT inactivator that would exhibit superior binding and enzyme inactivation when compared to vigabatrin. The development work ultimately culminated in the development of (1S,3S)-3-amino-4-difluoromethylenyl-1-cyclopentanoic acid (U.S. Pat. Nos. 6,794,413 and 7,381,748, referred to as compound 3 in the text below). The contents of U.S. Pat. Nos. 6,794,413 and 7,381,748 are expressly incorporated herein by reference. During this development process, several other candidate compounds were created, including (1R,4S)-4-amino-cyclopent-2-ene-1-carboxylic acid (compound 2 in Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293 and referred to as compound 1 in the text below) and (1S,3S)-3-amino-4-methylenyl-1-cyclopentanoic acid (compound 6 in Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293 and referred to as compound 2 or (1S,3S)-3-amino-4-methylenyl-1-cyclopentanoic acid in the text below). As published in 2003, Silverman, et. al. (Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293) stated that compound 1 "was not a GABA-AT inactivator but was a very good substrate with a specificity constant almost five times greater than that of GABA It was further implied that compound 1's failure to inhibit GABA-AT made it a poor candidate for further development as an antiepileptic medication" and work proceeded on a new candidate molecule. The next candidate molecule was Compound 2. As published in 2003 for Compound 2, "inactivation of GABA-AT was observed with 6, but when 2-mercaptoethanol was added to the incubation mixture, no inactivation occurred." Qiu, Jian; Pingsterhous, Joyce M.; Silverman, Richard B.; "Inhibition and Substrate Activity of Conformationally Rigid Vigbatrin Analogues with γ-Aminobutyric Acid Aminotransferase", J. Med. Chem., 1999, 42(22), 4725-4728. The same publication goes on to explain that the lack of activity in the presence of 2-mercaptoethanol is an indication that the GABA-AT first acts on Compound 2 to form an alpha-beta unsaturated ketone (3-oxo-4-methylenyl-1-cyclopentanoic acid, compound 8 in that publication). The mercaptoethanol then reacts with the alpha-beta unsaturated ketone before it can inactivate the enzyme. As published in 1991 (Burke, James R.; Silverman, Richard B.; "Mechanism of inactivation of γ-aminobutyric acid aminotransferase by the antiepilepsy drug γ-vinyl GABA (vigabatrin)", J. Am. Chem. Soc., 1991, 113(24), 9341-9349), the formation of this alpha-beta unsaturated ketone is one of the two pathways hypothesized to lead to the inactivation of GABA-AT.

(1S,3S)-3-amino-4-difluoro methylenyl-1-cyclopentanoic acid inhibits GABA-aminotransferase (GABA-AT), the enzyme responsible for the catabolism of GABA in the brain. Unlike the variety of GABA-ergic drugs that have been tried for treatment of tics (i.e. baclofen) which have met with very limited success, (1S,3S)-3-amino-4-difluoromethylenyl-1-cyclopentanoic acid is not expected to significantly raise GABA tone (a continuous background level of GABA signaling) in the brain. Instead, the inhibition of GABA-AT results in a build-up of GABA in presynaptic terminals of GABA-ergic neurons. These large stores of GABA, packaged in vesicles, are released when the GABA-ergic neuron is depolarized. As GABA-AT inhibition significantly increases the stores of GABA in the presynaptic terminal, when the neuron depolarizes and releases GABA, the GABA-ergic "signal" is significantly increased. In other words, (1S,3S)-3-amino-4-difluoromethylenyl-1-cyclopentanoic acid should effectively "amplify" the GABA-ergic signaling mechanisms without significantly raising GABA-tone.

In the case of GABA-ergic drugs that raise GABA tone, either by direct action on GABA receptors (i.e. baclofen) or by inhibition of GABA reuptake (i.e. tiagabine), increased GABA tone initiates adaptive mechanisms in the brain that lead to tolerance to the drug and an attenuation of the drug's effects, particularly in the dopaminergic neurons. Furthermore, continuous activation of GABA receptors leads to a variety of central nervous system (CNS) adverse effects. In contrast, (1S,3S)-3-amino-4-difluoromethylenyl-1-cyclopentanoic acid amplifies the GABA-ergic signaling without triggering adaptations to changes in GABA tone, and also has minimal CNS adverse effects as there is not continuous elevated GABA signaling. It is for this reason that (1S,3S)-3-amino-4-difluoromethylenyl-1-cyclopentanoic acid is believed to have a very benign CNS adverse effects profile, and why there is no significant development of tolerance to the effects of the drug.

The action of (1S,3S)-3-amino-4-difluoromethylenyl-1-cyclopentanoic acid is transient in nature. "Amplified" GABA signals are sent to the dopaminergic neuron, but the GABA signaling duration is not long enough to activate the compensatory mechanisms that blunt the dopaminergic neurons' response to GABA.

Given putative evidence that hyperfunction of dopaminergic neurotransmission and reduction/dysfunction of phasic GABAergic neurons in the CTSC tracts may underlie the pathophysiology of TD, (1S,3S)-3-amino-4-difluoromethylenyl-1-cyclopentanoic acid hydrochloride salt has theoretical potential to ameliorate tics in patients with TD. (1S,3S)-3-amino-4-difluoromethylenyl-1-cyclopentanoic acid's activity-dependent release of presynaptic GABA quenches the phasic increase in DA, and thus makes it potentially uniquely beneficial to patients with TD. However, the lack of efficacy data and safety data on (1S,3S)-3-amino-4-difluoromethylenyl-1-cyclopentanoic acid will require additional preclinical testing before beginning human clinical trials.

While the compound (1S,3S)-3-amino-4-difluoromethylenyl-1-cyclopentanoic acid hydrochloride salt has been shown to be a GABA aminotransferase inactivator like vigabatrin, surprisingly (1S,3S)-3-amino-4-difluoromethylenyl-1-cyclopentanoic acid hydrochloride salt does not inhibit the reuptake of GABA.

Materials:

Vigabatrin, (R)-baclofen, GABA, isoguvacine, sodium pyruvate, theophylline, gentamycin, and all buffer reagents were purchased from Sigma-Aldrich (St. Louis, Mo., USA). (1S,3S)-3-Amino-4-difluoromethylenyl-1-cyclopentanoic acid hydrochloride salt was synthesized as reported previously (Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293). [$^3$H]GABA (35 or 40.0 Ci/mmol) and [$^3$H]muscimol (36.6 Ci/mmol) were purchased from PerkinElmer (Boston, Mass., USA). All reagents for cell culturing were purchased from Invitrogen (Paisley, UK). Cocaine USP was provided by the National Institute on Drug Abuse (NIDA). All animals were adult male Sprague-Dawley rats (200-225 g, supplied by Taconic Farms, Germantown, N.Y.).

GABA Uptake Assay

[$^3$H]GABA Uptake Assay at Human GABA Transporters tsA201 cells were cultured in GlutaMAX-I DMEM supplemented with 10% fetal bovine serum, penicillin (100 U/ml), and streptomycin (100 µg/ml) at 37° C. in a humidified atmosphere of 95% air and 5% $CO_2$. The plasmids encoding hGAT-1, hBGT-1, hGAT-2, and hGAT-3, (Kvist, T.; Christiansen, B.; Jensen, A. A.; Bräuner-Osborne, H. The four human gamma aminobutyric acid (GABA) transporters: pharmacological characterization and validation of a highly efficient screening assay. Comb. Chem. High Throughput Screen 2009, 12, 241-249) respectively, were transfected into tsA201 cells using PolyFect according to the protocol of the manufacturer (Qiagen, West Sussex, UK). The next day, the tsA201 cells transiently expressing each of the four human GABA transporter subtypes were split into poly-D-lysine-coated white 96-well plates (PerkinElmer). The pharmacological assays were performed 36-48 h after transfection exactly as described previously (Christiansen, B.; Meinild, A. K.; Jensen, A. A; Bräuner-Osborne, H. Cloning and characterization of a functional human gamma-aminobutyric acid (GABA) transporter, human GAT-2. J. Biol. Chem. 2007, 282, 19331-19341). In brief assay buffer supplemented with 30 nM [$^3$H]GABA and test compounds was added to the cells, and the uptake of [$^3$H]GABA was determined after incubation at 37° C. for 3 min. Quantification was performed by using Microscint™ 20 scintillation fluid (Perkin Elmer) and a Packard TopCount microplate scintillation counter.

[³H]GABA Uptake Assay at Mouse GABA Transporters

Cortical astrocytes were cultured essentially as previously described (Hertz L, Juurlink B H J, Hertz E, Fosmark H and Schousboe A, Preparation of Primary Cultures of Mouse (Rat) Astrocytes, in A Dissection and Tissue Culture Manual of the Nervous System (Shahar A, de Vellis J, Vernadakis A and Haber B eds) pp 105-108, Alan R. Liss, Inc., New York, 1989). The neopallium was removed from new born NMRI mice (Taconic, Denmark) and passed through an 80 μm nylon sieve and cultured in modified Dulbecco's modified Eagle's medium with fetal calf serum. The calf serum was lowered from 20% to 10% over three weeks, and finally the astrocytes were allowed to differentiate using 0.25 mM dibutyryl cyclic AMP during the last week of growth.

Cortical neurons were cultured essentially as previously described by removing the neopallium of 15-day old NMRI embryos by dissection followed by mild trypsination (Hertz E, Yu A C H, Hertz L, Juurlink B H J and Schousboe A. Preparation of Primary Cultures of Mouse Cortical Neurons, in A Dissection and Tissue Culture Manual of the Nervous System (Shahar A, de Vellis J, Vernadakis A and Haber B eds) pp 183-186, Alan R. Liss, Inc., New York, 198). The neurons were cultured in 10% fetal calf serum and, after 48 h, cytosine arabinoside was added to a final concentration of 20 μM to prevent glial proliferation. Four cultures of stably transfected Human Embryonic Kidney (HEK)-293 cells expressing mGAT1-4 were prepared by the method previously reported (White H S, Sarup A, Bolvig T, Kristensen A S, Petersen G, Nelson N, Pickering D S, Larsson O M, Frølund B, Krogsgaard-Larsen P and Schousboe A. Correlation Between Anticonvulsant Activity and Inhibitory Action on Glial Gamma-Aminobutyric Acid Uptake of the Highly Selective Mouse Gamma-Aminobutyric Acid Transporter 1 Inhibitor 3-Hydroxy-4-Amino-4,5,6,7-Tetrahydro-1,2-Benzisoxazole and Its N-Alkylated Analogs. *J Pharmacol Exp Ther.* 2002, 302, 636-644). The stable cell lines are under the selection pressure of blasticidin-S at 5 μg/mL. Determinations of the $IC_{50}$ values were conducted as described earlier (Bolvig T, Larsson O M, Pickering D S, Nelson N, Falch E, Krogsgaard-Larsen P and Schousboe A. Action of Bicyclic Isoxazole GABA Analogues on GABA Transporters and Its Relation to Anticonvulsant Activity. *Eur. J. Pharmacol.* 1999, 375, 367-374). In brief [³H]GABA uptake was assessed at 37° C. for 3 min on desired cells in PBS buffer containing 1 μM GABA, 13 nM [³H]GABA, and test compound. Radioactivity was measured using Microscint™ 20 scintillation fluid (PerkinElmer) and a Packard TopCount microplate scintillation counter.

GABA Receptor Binding Assays

Receptor Preparations $GABA_A$ and $GABA_B$ binding assays were performed using rat brain synaptic membranes of cortex and the central hemispheres from adult male Sprague-Dawley rats with tissue preparation as earlier described (Ransom, R. W.; Stec, N. L. Cooperative modulation of [³H]MK-801 binding to the N-methyl-D-aspartate receptor-ion channel complex by L-glutamate, glycine, and polyamines. *J. Neurochem.* 1988, 51, 830-836). On the day of the assay, the membrane preparation was quickly thawed, suspended in 40 volumes of ice-cold 50 mM Tris-HCl buffer (pH 7.4) using an UltraTurrax homogenizer and centrifuged at 48,000 g for 10 min at 4° C. This washing step was repeated four times. The final pellet was resuspended in incubation buffer and the binding assay carried out as detailed below.

$GABA_A$ Receptor Activity Assay

Rat brain synaptic membranes (100 μg protein/aliquot) prepared above in Tris-HCl buffer (50 mM, pH 7.4) were incubated with [³H]muscimol (5 nM) and 100 μM of compound 2 at 0° C. for 60 min in a total volume of 250 μl. GABA (1 mM) was used to define non-specific binding. The binding reaction was terminated by rapid filtration through GF/B unifilters (PerkinElmer) using a 96-well Packard FilterMate cell harvester, followed by washing with 3×250 μl of ice-cold binding buffer, drying, and adding scintillation fluid, as described for the [³H]GABA uptake assay.

$GABA_B$ Receptor Binding Assay

For [³H]GABA binding to the $GABA_B$ receptors, rat brain synaptic membranes (200 μg protein/aliquot) were suspended in Tris-HCl buffer (50 mM+2.5 mM CaCl$_2$, pH 7.4) and incubated with [³H]GABA (5 nM), isoguvacine (40 μM), and 100 μM of compound 2 at 25° C. for 45 min in 1 ml total volume. Isoguvacine serves to saturate $GABA_A$ receptors (Hill, D. R.; Bowery, N. G. ³H-baclofen and ³H-GABA bind to bicuculline-insensitive $GABA_B$ sites in rat brain. *Nature* 1981, 290, 149-152). Non-specific binding was determined using 100 μM (R)-baclofen. Binding was terminated by filtration through Whatman GF/C filters, using a Brandell M-48R Cell Harvester; filters were washed with 3×3 ml of ice-cold buffer, and filter-bound radioactivity was counted in a Packard Tricarb 2100 liquid scintillation analyzer using 3 ml of Opti-fluor scintillation fluid (PerkinElmer).

Interaction of (1S,3S)-3-amino-4-difluoromethylenyl-1-cyclopentanoic acid hydrochloride salt with GABA Receptors To investigate a possible interaction of (1S,3S)-3-amino-4-difluoromethylenyl-1-cyclopentanoic acid hydrochloride salt with GABA receptors, the compound was tested for its ability to displace [³H]GABA binding to ionotropic $GABA_A$ receptors or metabotropic $GABA_B$ receptors in rat brain cortical homogenate. At a concentration of 100 μM, no inhibition of binding was observed at either receptor tested, whereas 1 mM cold GABA inhibited radioligand binding as expected (Table 3). Furthermore, (1S,3S)-3-amino-4-difluoromethylenyl-1-cyclopentanoic acid hydrochloride salt was tested for activity at recombinant human ρ1 $GABA_C$ receptors expressed in oocytes and was found to exhibit no effect as an agonist or antagonist at a concentration of 100 μM.

TABLE 3

Effect of (1S,3S)-3-amino-4-difluoromethylenyl-1-cyclopentanoic acid on $GABA_A$ and $GABA_B$ receptors evaluated in binding assays

| | $IC_{50}$ (μM) | |
|---|---|---|
| | (1S,3S)-3-amino-4-difluoromethylenyl-1-cyclopentanoic acid | GABA |
| [³H]muscimol competition ($GABA_A$ receptor) | >100 | 0.049[a] |
| [³H]GABA competition[b] ($GABA_B$ receptor) | >100 | 0.013[a] |

[a]data from Wellendorph, P.; Høg, S.; Greenwood, J. R.; de Lichtenberg, A.; Nielsen, B.; Frølund, B.; Brehm, L.; Clausen, R. P.; Bräuner-Osborne, H. Novel cyclic gamma-hydroxybutyrate (GHB) analogs with high affinity and stereoselectivity of binding to GHB sites in rat brain. *J. Pharmacol. Exp. Ther.* 2005, 315, 346-351.
[b]a high concentration of isoguvacine was added to ensure saturation of $GABA_A$ receptor sites Vigabatrin inhibits GABA uptake (Ludwig et al, Inhibition of uptake, steady-state currents, and transient charge movements generated by the neuronal GABA transporter by various anticonvulsant drugs. Br J Pharmacol. 1999 September; 128(1):92-102), Therefore it has been surprisingly discovered that the vigabatrin derivative (1S,3S)-3-amino-4-difluoromethylenyl-1-cyclopentanoic acid hydrochloride salt does not inhibit [³H]GABA uptake in neurons, astrocytes, or mammalian cells recombinantly expressing the four different human GABA transporter subtypes (hGAT-1, hBGT-1, hGAT-2, and hGAT-3), nor does it bind to $GABA_A$ or $GABA_B$ receptors in rat brain homogenate, or affect GABA$_C$ receptor activity in *Xenopus laevis* oocytes. Thus, it appears that (1S, 3S)-3-amino-4-difluoromethylenyl-1-cyclopentanoic acid hydrochloride salt is selective for GABA-AT.

Dosages of (1S,3S)-3-amino-4-difluoromethylenyl-1-cyclopentanoic acid, hydrochloride salt, are anticipated to be between 0.7 and 1000 mg/day (adults dosage), or 0.01 mg/kg/day to 15 mg/kg/day, for treatment of Tourette's Disorder. It is anticipated that a preferred clinical dose will be 5-25 mg/day for a normal weight adult.

Summary of Study Design:

This is an open label investigation to obtain preliminary data regarding dosage and tolerability of (1S,3S)-3-amino-4-difluoromethylenyl-1-cyclopentanoic acid hydrochloride salt in 6-10 subjects at least 18 years of age who meet Diagnostic and Statistical Manual of Mental Disorders, Text Revision (DSM-IV-TR, 2000) criteria for TD and who have had unsatisfactory response to prior treatments. Our goal is to obtain preliminary data on effect size for tics using Cohen's d, calculating the difference between the two means (baseline and endpoint scores on the Yale Global Tic Severity Scale (Y-GTSS), divided by the standard deviation of the difference.

Summary of Inclusion and Exclusion Criteria:

Subjects must be physically healthy, of at least average intelligence, and have no other significant medical or comorbid psychiatric disorders that are the primary focus of treatment.

Inclusion Criteria:

Subjects will be eligible for inclusion in this study if they meet all of the following criteria:

1. Subjects must be 18 years of age (inclusive) when informed consent is obtained.
2. Subjects must meet full DSM-IV diagnostic criteria for TD by clinical interview on examination by a physician investigator, and confirmed by the Structured Clinical Interview for DSM (SCID-CT) for clinical trials.
3. Subjects will have failed to respond to an adequate trial, as determined by the investigator, of clonidine, guanfacine, and a first generation (typical) and second generation (atypical) neuroleptic medication in the past.
4. Tics are causing significant distress or impairment, as determined by the subject and principal investigator, on the current treatment regimen.
5. Laboratory results, including serum chemistries, hematology, and urinalysis, must show no significant abnormalities (significant is defined as laboratory values requiring acute medical intervention).
6. Subjects will not undergo formal IQ testing, but must be of normal intelligence in the judgment of the investigator.
7. Subjects must possess an educational level, degree of understanding and command of the English language to enable them to communicate suitably with the investigators and study coordinator, and to understand the nature of the study.
8. Subjects must be considered reliable.
9. Written informed consent of subjects is obtained.

Exclusion Criteria:

Subjects will be excluded from the study for any of the following reasons:

1. Subjects with organic brain disease, for example, traumatic brain injury residua.
2. Subjects meeting criteria for mental retardation as defined by the DSM-IV-TR.
3. Subjects with a history of seizure disorder (other than febrile seizure).
4. Subjects with history of Sydenham's Chorea.
5. Subjects with autism, schizophrenia, other psychotic disorder, or bipolar disorder.
6. Subjects with a primary diagnosis of a major mood disorder that requires ongoing psychiatric treatment.
7. Subjects with a neurological disorder other than a tic disorder.
8. Subjects with a major medical illness.
9. Female subjects who are unwilling to use birth control or who are pregnant, as determined by serum pregnancy test at baseline assessment, or lactating.
10. Subjects who have a past or current history of substance dependence and/or a current history of substance abuse or who fail baseline toxicology screen.
11. Subjects who have any clinically significant abnormal laboratory result at baseline screening including EKG, or blood tests.
12. Subjects who, in the opinion of the investigator, are unsuitable in any other way to participate in this study.
13. Subjects that are currently taking Vigabatrin (Sabril™) for the treatment of epilepsy.

Proposed Visit Schedule:

The trial will last approximately 8 weeks and include 8 visits. Assessment visits will take place at baseline (Visit 1), and treatment weeks 0 (visit 2), 1 (visit 3), 2 (visit 4), 3 (visit 5) 4 (visit 6), 6 (visit 7) and 8 (visit 8).

Visit 1 (Baseline Assessment and Medication Washout):

After pre-screening, at this visit written consent, baseline physical exam, vital signs, height and weight, EKG, and laboratory assessment will be conducted. Clinical assessment will consist of clinical evaluation by the co-principal investigator experienced in the evaluation and treatment of Tourette's and tic disorders (BC), and semi-structured diagnostic interview (SCID-CT).

Taper and Discontinuation of Previous Tic Medication.

Current tic medication will be tapered and discontinued. Visit 1 may be divided into additional visits (i.e. 1A, 1B) to taper and withdraw previous tic medication if needed. Subjects must be off all other tic medications prior to beginning treatment with (1S,3S)-3-amino-4-difluoromethylenyl-1-cyclopentanoic acid hydrochloride salt by Study Visit 2. If feasible, subjects should be off clonidine or guanfacine for at least 2 weeks, and typical or atypical neuroleptics for at least 4 weeks prior to starting the study medication. However, if it is clinically unfeasible, in the judgment of the investigator, for the subject to remain off previous tic medication for the duration of the discontinuation phase, (1S,3S)-3-amino-4-difluoromethylenyl-1-cyclopentanoic acid hydrochloride salt may be initiated before the end of the 2-4 week period, with agreement of the subject and investigator.

In regard to taper and discontinuation of previous medications, clinically unfeasible is defined as: in the judgment of investigator, the subject's tics would be highly likely to cause increased distress or impairment to the subject without treatment and initiation of treatment with a replacement therapy, in this case (1S,3S)-3-amino-4-difluoromethylenyl-1-cyclopentanoic acid hydrochloride salt, would be indicated.

Medication for Psychiatric Comorbid Conditions. Subjects on medications for a comorbid condition (such as a stimulant for ADHD or a selective serotonin reuptake inhibitor (SSRI) for OCD) may remain on the medication during the study, but will agree to remain on the same dosage throughout the duration of the study.

Baseline Measures:

The following instruments will be used to assess diagnosis and symptom severity at baseline:

a) SCID-CT. A clinician administered, semi-structured diagnostic interview specifically developed for use in clinical trials with adults
b) Yale Global Tic Severity Scale (Y-GTSS) (Leckman et al, 1989). The primary outcome measure for tic assessment is this investigator administered Global Severity score (sum of Total Tic score and TD Impairment score) on the Y-GTSS. It includes measures of tic frequency and severity and is widely used in drug efficacy trials involving TD.
c) Yale-Brown Obsessive Compulsive Scale (Y-BOCS) (Goodman et al, 1989). The Y-BOCS is a primary outcome measure of OCD symptoms and is rated by a study investigator.
d) Clinical Global Impression for Tics (Tics-CGI) (Leckman et al, 1988), for ADHD (ADHD-CGI), and for OCD (OCD-CGI) (Guy et al, 1976). Rated by the investigator. Global Improvement (1=very much improved, to 7=very much worse) scales. At intake, only the severity can be rated. In subsequent assessments, both severity and improvement will be rated. A CGI improvement of 1 (very much) or 2 (much) improved is considered to be an acceptable response to acute treatment as is a clinical severity rating of ≤3.
e) DSM-IV-TR Global Assessment of Functioning Scale (GAF) (APA DSM-IV-TR, 2000). The investigator-rated GAF ranges from 1-100, with scores over 70 indicating normal adjustment, and below 60, clinically significant impairment.
f) Hamilton Depression Scale. A clinician-rated scale used as a screening and diagnostic tool and a measure of severity of depression in adults, which has been widely used in clinical trials of young adults with MDD.
g) Hamilton Anxiety Scale. A clinician-rated scale used as a screening and diagnostic tool and a measure of severity of depression in adults, which has been widely used in clinical trials of young adults with MDD.
h) Conners Adult ADHD Rating Scale (CAARS:SL) Systematic self report of ADHD symptoms in adults.
i) Adverse Events Form (SMURF) is completed at every visit to document all adverse events that occur during the study.
j) Demographics: Demographics and family history information are collected systematically during the Screening/Baseline Phase.
k) Vital signs, Weight and Height (pulse, blood pressure, weight, and height) will be assessed at every visit.
l) Abnormal Involuntary Movement Scale (AIMS) An investigator rated scale of abnormal involuntary movements including tardive dyskinesia.
m) Opthalmological evaluation including visual fields testing Visit 2 (Treatment Week 0):

Clinical Assessment (See Table 4). Subjects will undergo a repeat assessment of all baseline rating scales, except for the SCID-CT, physical exam and Demographics Assessment. Vital signs, weight, height, AIMS and adverse events will be assessed at every visit.

Subjects will be started on (1S,3S)-3-amino-4-difluoromethylenyl-1-cyclopentanoic acid hydrochloride salt according to dosing plan 1 (see Table 5). Based on the known dose-effects profile of this drug, dosing plan 1 is the most clinically useful dosing regimen. Due to the mechanism of action of (1S,3S)-3-amino-4-difluoromethylenyl-1-cyclopentanoic acid hydrochloride salt and the relatively long period of time (several days) for the denovo resynthesis of GABA-aminotransferase, it is envisioned that dosing regimens using smaller doses of this drug will be effective in the treatment of Tourette's Disorder because less drug would be effective at maintaining a low GABA-aminotransferase activity after initial depletion of enzyme activity. In addition, the treatment of Tourette's Disorder in some patients may require both the GABA-aminotransferase inactivation capability of (1S,3S)-3-amino-4-difluoromethylenyl-1-cyclopentanoic acid hydrochloride salt that occurs at doses below 1 mg/kg and the somnolence or sedative behavior of this drug, that occurs at higher doses. Therefore, it is envisioned that other dosing regimens with a high maximum dose will be both effective and necessary for the treatment of some patients. The alternative dosing plans envisioned to be effective can be found in Table 5. However, due to the known somnolence side effect upon initiation of treatment, and the known dose at which this effect is observed, the initial dose on week zero is not equally proportional to the maximum dose utilized during the study for all dosing plans.

Visit 3 (Treatment Week 1):

Clinical Reassessment (see Table 4). Vital signs, weight, height, AIMS and adverse events will be assessed at each visit. Visit 3 will also include: Yale Global Tic Severity Scale (Y-GTSS), Clinical Global Impression for Tics (Tic-CGI), ADHD (ADHD-CGI) and OCD (OCD-CGI), Global Assessment of Functioning Scale (GAF)

Visit 4 (Treatment Week 2):

Clinical reassessment (See Table 4). Vital signs, weight, height, AIMS and adverse events will be assessed at each visit. Visit 4 will further include Yale Global Tic Severity Scale (Y-GTSS), Clinical Global Impression for Tics (Tics-CGI), ADHD (ADHD-CGI) and OCD (OCD-CGI), Y-BOCS, CAARS, and GAF.

Visit 5: (Treatment Week 3):

Clinical Reassessment (See Table 4). Vital signs, weight, height, AIMS and adverse events will be assessed at each visit. Visit 5 will further include Yale Global Tic Severity Scale (Y-GTSS); Clinical Global Impression for TS (TS-CGI), ADHD (ADHD-CGI) and OCD (OCD-CGI); GAF; Adverse Events Form (SMURF)

Visit 6 (Treatment Week 4)

Clinical Reassessment (See Table 4). Vital signs, weight, height, AIMS and adverse events will be assessed at each visit. Visit 6 will further include: Yale Global Tic Severity Scale (Y-GTSS); Yale-Brown Obsessive Compulsive Scale (Y-BOCS), CAARS; Clinical Global Impression for Tics (Tics-CGI), ADHD (ADHD-CGI) and OCD (OCD-CGI), GAF, Adverse Events Form (SMURF)

Visit 7 (Treatment Week 6)

Clinical Reassessment (See Table 4). Vital signs, weight, height, AIMS and adverse events will be assessed at each visit. Visit 7 will also include: Yale Global Tic Severity Scale (Y-GTSS), Clinical Global Impression for Tics (Tics-CGI), ADHD (ADHD-CGI) and OCD (OCD-CGI), and GAF.

Visit 8 (Treatment Week 8)

Clinical Assessment (See Table 4). Subjects will undergo an endpoint, repeat assessment of all baseline rating scales, except for the SCID-CT and Demographics Assessment. Endpoint outcome measures will be calculated.

TABLE 4

TASKS BY VISIT

| Assessment Tools | Baseline visit 1 | Week 0 visit 2 | Week 1 visit 3 | Week 2 visit 4 | Week 3 visit 5 | Week 4 visit 6 | Week 6 visit 7 | Week 8 visit 8 |
|---|---|---|---|---|---|---|---|---|
| | | | | Screen Phase | | | | |
| SCID-CT | X | | | | | | | |
| Y-GTSS | X | X | X | X | X | X | X | X |
| Y-BOCS | X | X | | X | | X | | X |
| CGI-Tics | X | X | X | X | X | X | X | X |
| CGI-OCD | X | X | X | X | X | X | X | X |
| CGI-ADHD | X | X | X | X | X | X | X | X |
| GAF | X | X | X | X | X | X | X | X |
| HAM-D | X | X | | | | | | X |
| HAM-A | X | X | | | | | | X |
| CAARS | X | X | | X | | X | | X |
| Adverse Events | X | X | X | X | X | X | X | X |
| Physical Exam | X | | | | | | | |
| Weight and Height | X | X | X | X | X | X | X | X |
| Blood Tests: CBC, Metabolic Panel including Liver Function Tests, Cholesterol, Triglycerides, Fasting Blood Sugar and Prolactin | X | | | | | | | X |
| ECG | X | | | | | | | X |
| Urine toxic screen | X | | | | | | | |
| Pregnancy test (females only) | X | | | | | | | |
| Vital Signs | X | X | X | X | X | X | X | X |
| AIMS | X | X | X | X | X | X | X | X |

TABLE 5

DRUG DOSING PLANS
Dosing is envisioned to be administration of the complete daily dose at bedtime (hora somni or h.s.).

| Study | Dosing plans, milligrams per day of (1S,3S)-3-amino-4-difluoromethylenyl-1-cyclopentanoic acid, hydrochloride salt | | | | | | |
|---|---|---|---|---|---|---|---|
| Week | Plan #1 | Plan #2 | Plan #3 | Plan #4 | Plan #5 | Plan #6 | Plan #7 |
| 0 | 25 | 5 | 10 | 5 | 0.7 | 25 | 25 |
| 1 | 25 | 10 | 10 | 5 | 0.7 | 150 | 200 |
| 2 | 25 | 25 | 10 | 5 | 0.7 | 500 | 1000 |
| 3 | 25 | 25 | 10 | 5 | 0.7 | 500 | 1000 |
| 4 | 25 | 25 | 10 | 5 | 0.7 | 500 | 1000 |
| 5 | 25 | 25 | 10 | 5 | 0.7 | 500 | 1000 |
| 6 | 25 | 25 | 10 | 5 | 0.7 | 500 | 1000 |
| 7 | 25 | 25 | 10 | 5 | 0.7 | 500 | 1000 |
| 8 | 25 | 10 | 10 | 5 | 0.7 | 150 | 200 |

Follow-Up:

Subjects enrolled in the study will be eligible for follow-up at the NYU Clinical and Research Program for Tics and Tourette's following completion of the study. Those who show benefit from the medication at the endpoint dosage may have the opportunity to continue treatment, but at a reduced dose and with appropriate follow up testing, including visual fields assessments every four months.

Data Analysis:

As this is a preliminary, open label study to systematically assess safety, all analyses will be descriptive. Patient characteristics for all individuals enrolled in the study will be summarized.

Analysis of safety data will include all subjects who take at least one dose of study medication. Types and percentages of treatment-emergent, unsolicited adverse effects will be summarized for each visit. Any subject who experiences a serious adverse effect, or who cannot tolerate any adverse effect, will be taken off the medication and removed from the study.

To obtain preliminary data regarding effect size, we will examine mean change from baseline to endpoint on measures of tics (Y-GTSS). We will obtain preliminary data on effect size (ES) for tics using Cohen's d, calculating the difference between the two means (baseline and endpoint scores on the Y-GTSS), divided by the standard deviation of the difference. Exploratory analyses will take place with change from baseline on CGI-Tics Severity, and Y-BOCS, CAARS, Hamilton A and D. Although our mean baseline and endpoint scores are non-independent, if the pooled standard deviation is corrected for the amount of correlation between measures, then the ES estimate will be an overestimate of the actual ES (Dunlop, Cortina, Vaslow and Burke, 1996). Thus, we will use the original standard deviations.

Minimizing Risk of Intolerable Increase in Tics During Taper and Discontinuation Phase of Previous Tic Medication If tics increase to the point of causing significant distress or impairment to the subject, by clinical judgment of the investigator and subject, appropriate measures will be instituted to reduce the symptoms. Measures to reduce symptoms could include 1) initiation of (1S,3S)-3-amino-4-difluoromethylenyl-1-cyclopentanoic acid hydrochloride salt before the end of the discontinuation phase of previous tic medication if tics worsen during the discontinuation phase, 2) adjustment in dose of (1S,3S)-3-amino-4-difluoromethylenyl-1-cyclopentanoic acid hydrochloride salt as needed during the treatment phase, or 3) removal of the subject from the study if tics worsen on two consecutive treatment visits.

Clinical Observations

A single patient diagnosed with Tourettes's Disorder (TD) was treated with vigabatrin for a period of about ten months. Subject is a 33 year old man with a longstanding history of severe TD. His course was characterized by typical attenuation of symptoms in late adolescence/early adulthood with an unusual, but not rare, acceleration of symptoms to lifetime peak severity in the last several years. This exacerbation occurred in temporal association with several significant life stressors. Marking the severity of his TD course was a history of fractured rib secondary to a truncal tic, inability to take public transportation, and inability to find steady work in his profession. He had been treated with many medications since adolescence for his severe tics, and either failed to respond or was unable to tolerate any of them. He was on tetrabenazine at the time of referral to the study, but his response to this medication was limited by depressed mood symptoms and moderate fatigue.

Figure 1:
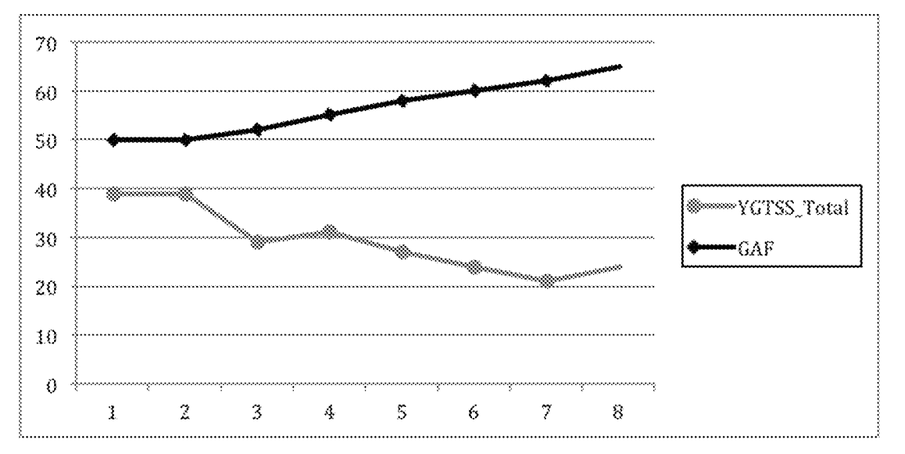
FIG. 1 is a graph showing the Baseline Yale Global Tic Severity Score and Global Assessment of Functioning Score of a patient.

Baseline Yale Global Tic Severity Score (YGTSS) score indicated a total motor score of 22, and a total vocal score of 17, for a total tic score (TTS) of 39 and a tic-related impairment score of 40; global severity was 79. Global Assessment of Functioning (GAF) score at baseline was 50.

YGTSS TTS scores during treatment are attached. TTS decreased to 29 at vigabatrin (GVG), gram (week 1), to 31 at GVG 2 grams (week 2), 27 at GVG 3 grams (week 3), 24 at GVG 3 grams (week 4), 21 at GVG 3 grams (week 5) and 24 at GVG 3 grams (week 7). GAF scores increased to 65 at week 7, as the subject was able to begin to use public transportation, and look for employment.

Adverse effect of GVG was minimal: tiredness and fatigue starting at 2 grams, which gradually attenuated. His eye exam at 7 weeks was normal, and showed no change from baseline.

In summary, this subject has experienced clinically significant and meaningful improvement in his tic severity as a result of GVG treatment, with mild and non-limiting adverse effect of fatigue. His eye exams have remained unchanged and within normal limits.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

American Psychiatric Association. Diagnostic and Statistical Manual. Fourth Edition, Text Revision. American Psychiatric Association Press, 2000.
Albin, R. Neurobiology of Basal Ganglia and TS. Abstract, International Tourette Syndrome Association Scientific Meeting, June 26, Cleveland, Ohio
Coffey B, Biederman J, Spencer T, Geller D, Faraone S, Bellordre, C.
Informativeness of Structured Diagnostic Interviews in the Identification of Tourette's Disorder in Referred Youth. Journal of Nervous and Mental Disease 2000, 188: 583-588.
Green, Wayne. Antipsychotic Drugs. Child and Adolescent Clinical Psychopharmacology, Lippincott, Williams and Wilkins, Philadelphia, p. 89-14; 2001
Dunlop, W. Cortina, J., Vaslow, Land Burke, M. Meta-analysis of experiments with matched groups or repeated measures designs Psychological Methods, 1, 170-177, 1996

We claim:

1. A method of treating Tourettes Disorder (TD) comprising elevating the build-up of GABA in presynaptic terminals of GABA-ergic neurons.

2. The method of claim 1 wherein the GABA levels are elevated by administration of an effective amount of vigabatrin or (1S,3S)-3-amino-4-methylenyl-1-cyclopentanoic acid, or a pharmaceutically acceptable salt thereof.

3. The method of claim 2 wherein the salt is selected from the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate, amino acids, aluminum, calcium, lithium, magnesium, potassium, sodium, zinc, or diethanolamine salts.

4. A method of treating Tourette's Disorder (TD) comprising elevating the GABA in presynaptic terminals of GABA-ergic neurons without significantly elevating the background level of GABA in the brain.

5. The method of claim 4 wherein the GABA levels are elevated by administration of an effective amount of vigabatrin or (1S,3S)-3-amino-4-methylenyl-1-cyclopentanoic acid, or a pharmaceutically acceptable salt thereof.

6. The method of claim 5 wherein the salt is selected from the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate, amino acids, aluminum, calcium, lithium, magnesium, potassium, sodium, zinc, or diethanolamine salts.

7. A method of treating Tourette's Disorder (TD) comprising the administration of an effective amount of a GABA-aminotransferase inactivator.

8. The method of claim 7 wherein the GABA-aminotransferase inactivator is selected from vigabatrin or (1S,3S)-3-amino-4-methylenyl-1-cyclopentanoic acid.

9. The method of claim 7 wherein the GABA-aminotransferase inactivator is vigabatrin or a pharmaceutically acceptable salt thereof.

10. The method of claim 9 wherein the salt is a hydrochloride salt.

11. The method of claim 9 wherein the salt is selected from the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate, amino acids, aluminum, calcium, lithium, magnesium, potassium, sodium, zinc, or diethanolamine salts.

12. The method of claim 9 wherein the vigabatrin is administered daily at a dose between 0.5 and 4 grams.

13. The method of claim 9 wherein the vigabatrin is administered at 1 gram/day for the first week, 2 grams/day for the second week, administered at 3 grams/day for the third, fourth, fifth, sixth, and seventh weeks, 2 grams/day for the eighth week, and 1 gram/day for the ninth week of treatment.

14. The method of claim 8 wherein the GABA-aminotransferase inactivator is (1S,3S)-3-amino-4-methylenyl-1-cyclopentanoic acid or a pharmaceutically acceptable salt thereof.

15. The method of claim 14 wherein the salt is a hydrochloride salt.

16. The method of claim 14 wherein the salt is selected from the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate, amino acids, aluminum, calcium, lithium, magnesium, potassium, sodium, zinc, or diethanolamine salts.

17. The method of claim 14 wherein the (1S,3S)-3-amino-4-methylenyl-1-cyclopentanoic acid is administered daily at a dose between 0.7 and 1000 milligrams.

18. The method of claim 14 wherein the (1S,3S)-3-amino-4-methylenyl-1-cyclopentanoic acid is administered at 25 milligrams/day for the first week, 150 milligrams/day for the second week, administered at 500 milligrams/day for the third, fourth, fifth, sixth, seventh, and eighth weeks, and 150 milligrams/day for the ninth week of treatment.

19. The method of claim 14 wherein the (1S,3S)-3-amino-4-methylenyl-1-cyclopentanoic acid is administered at 5 milligrams/day for the first week, 10 milligrams/day for the second week, administered at 25 milligrams/day for the third, fourth, fifth, sixth, seventh, and eighth weeks, and 10 milligrams/day for the ninth week of treatment.

20. The method of claim 14 wherein the (1S,3S)-3-amino-4-methylenyl-1-cyclopentanoic acid is administered at 25 milligrams/day for 9 consecutive weeks.

21. The method of claim 14 wherein the (1S,3S)-3-amino-4-methylenyl-1-cyclopentanoic acid is administered at 10 milligrams/day for 9 consecutive weeks.

22. A method of treating Tourette's Disorder (TD) comprising the administration of an effective amount of vigabatrin.

23. The method of claim 22 wherein the vigabatrin is administered daily at a dose between 0.25 and 4 grams.

24. The method of claim 22 wherein the vigabatrin is administered at 1 gram/day for the first week, 2 grams/day for the second week, administered at 3 grams/day for the third, fourth, fifth, sixth, and seventh weeks, 2 grams/day for the eighth week, and 1 gram/day for the ninth week of treatment.

25. A method of treating Tourette's comprising the administration of an effective amount of (1S,3S)-3-amino-4-methylenyl-1-cyclopentanoic acid or a pharmaceutically acceptable salt thereof.

26. The method of claim 25 wherein the salt is a hydrochloride salt.

27. The method of claim 25 wherein the salt is selected from the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate, amino acids, aluminum, calcium, lithium, magnesium, potassium, sodium, zinc, or diethanolamine salts.

28. The method of claim 25 wherein the (1S,3S)-3-amino-4-methylenyl-1-cyclopentanoic acid is administered daily at a dose between 0.7 and 1000 milligrams.

29. The method of claim 26 wherein the (1S,3S)-3-amino-4-methylenyl-1-cyclopentanoic acid hydrochloride salt is administered daily at a dose between 0.7 and 1000 milligrams.

30. The method of claim 25 wherein the (1S,3S)-3-amino-4-methylenyl-1-cyclopentanoic acid is administered at 25 milligrams/day for the first week, 150 milligrams/day for the second week, administered at 500 milligrams/day for the third, fourth, fifth, sixth, seventh, and eighth weeks, and 150 milligrams/day for the ninth week of treatment.

31. The method of claim 26 wherein the (1S,3S)-3-amino-4-methylenyl-1-cyclopentanoic acid hydrochloride salt is administered at 25 milligrams/day for the first week, 150 milligrams/day for the second week, administered at 500 milligrams/day for the third, fourth, fifth, sixth, seventh, and eighth weeks, and 150 milligrams/day for the ninth week of treatment.

32. The method of claim 25 wherein the (1S,3S)-3-amino-4-methylenyl-1-cyclopentanoic acid is administered at 5 milligrams/day for the first week, 10 milligrams/day for the second week, administered at 25 milligrams/day for the third, fourth, fifth, sixth, seventh, and eighth weeks, and 10 milligrams/day for the ninth week of treatment.

33. The method of claim 26 wherein the (1S,3S)-3-amino-4-methylenyl-1-cyclopentanoic acid hydrochloride salt is administered at 5 milligrams/day for the first week, 10 milligrams/day for the second week, administered at 25 milligrams/day for the third, fourth, fifth, sixth, seventh, and eighth weeks, and 10 milligrams/day for the ninth week of treatment.

34. The method of claim 25 wherein the (1S,3S)-3-amino-4-methylenyl-1-cyclopentanoic acid is administered at 25 milligrams/day for 9 consecutive weeks.

35. The method of claim 25 wherein the (1S,3S)-3-amino-4-methylenyl-1-cyclopentanoic acid is administered at 10 milligrams/day for 9 consecutive weeks.

36. The method of claim 26 wherein the (1S,3S)-3-amino-4-methylenyl-1-cyclopentanoic acid hydrochloride salt is administered at 25 milligrams/day for 9 consecutive weeks.

37. The method of claim 26 wherein the (1S,3S)-3-amino-4-methylenyl-1-cyclopentanoic acid hydrochloride salt is administered at 10 milligrams/day for 9 consecutive weeks.

* * * * *